United States Patent
Solacroup et al.

(10) Patent No.: US 10,519,479 B1
(45) Date of Patent: Dec. 31, 2019

(54) METHODS FOR MODIFYING GLYCOSYLATION USING MANGANESE

(71) Applicant: Ares Trading S.A., Aubonne (CH)

(72) Inventors: Thomas Solacroup, Blonay (CH); Matthieu Stettler, Vucherens (CH); Martin Jordan, Ecublens (CH); Hervé Broly, Chatel-St Denis (CH)

(73) Assignee: ARES TRADING S.A., Aubonne (CH)

( * ) Notice: Subject to any disclaimer, the term of this patent is extended or adjusted under 35 U.S.C. 154(b) by 166 days.

(21) Appl. No.: 15/457,624

(22) Filed: Mar. 13, 2017

Related U.S. Application Data (60) Provisional application No. 62/308,634, filed on Mar. 15, 2016.

(51) Int. Cl.
| | | |
|---|---|---|
| C12N 9/96 | (2006.01) | |
| C07K 16/00 | (2006.01) | |
| C12P 21/06 | (2006.01) | |
| C12P 21/04 | (2006.01) | |
| C12P 21/00 | (2006.01) | |
| C07K 16/24 | (2006.01) | |

(52) U.S. Cl.
CPC .......... *C12P 21/005* (2013.01); *C07K 16/241* (2013.01); *C07K 2317/14* (2013.01); *C07K 2317/41* (2013.01); *C07K 2317/515* (2013.01); *C12N 2500/12* (2013.01)

(58) Field of Classification Search
None
See application file for complete search history.

(56) References Cited

U.S. PATENT DOCUMENTS

| | | | | |
|---|---|---|---|---|
| 7,863,426 B2* | 1/2011 | Wan | ......................... | C07K 1/18 530/390.1 |
| 7,972,810 B2* | 7/2011 | Crowell | ............... | C07K 14/505 435/69.1 |
| 2012/0276631 A1* | 11/2012 | Bengea | ................ | C07K 16/241 435/404 |

* cited by examiner

*Primary Examiner* — Yong D Pak
(74) *Attorney, Agent, or Firm* — Fox Rothschild LLP (57) ABSTRACT

The present invention relates to a cell culture method for adjusting the proportion of G0, G1, G2, and high-mannose galactosylation variants in a population of a recombinant protein produced by a culture of cells in a cell culture medium by supplementing the cell culture medium with manganese at one or more days of the cell culture method duration.

15 Claims, 1 Drawing Sheet
Specification includes a Sequence Listing.

SEQUENCE LISTING

```
<160> NUMBER OF SEQ ID NOS: 10

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variabe region

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
```

```
<213> ORGANISM: Artificial Sequence
<220> FEATURE:
<223> OTHER INFORMATION: adalimumab light chain variable region CDR3
<220> FEATURE:
<221> NAME/KEY: misc_feature
<222> LOCATION: (9)..(9)
<223> OTHER INFORMATION: Xaa can be any naturally occurring amino acid

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: misc_feature
<222> LOCATION: (12)..(12)
<223> OTHER INFORMATION: Xaa can be any naturally occurring amino acid

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
1               5                   10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
1               5                   10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1
```

```
<400> SEQUENCE: 8

Asp Tyr Ala Met His
1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtagggga cagagtcacc     60
atcacttgtc gggcaagtca gggcatcaga aattacttag cctggtatca gcaaaaacca   120
gggaaagccc ctaagctcct gatctatgct gcatccactt tgcaatcagg ggtcccatct   180
cggttcagtg gcagtggatc tgggacagat ttcactctca ccatcagcag cctacagcct   240
gaagatgttg caacttatta ctgtcaaagg tataaccgtg caccgtatac ttttggccag   300
gggaccaagg tggaaatcaa a                                              321

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc     60
tcctgtgcgg cctctggatt cacctttgat gattatgcca tgcactgggt ccggcaagct   120
ccagggaagg gcctggaatg ggtctcagct atcacttgga atagtggtca catagactat   180
gcggactctg tggagggccg attcaccatc tccagagaca acgccaagaa ctccctgtat   240
ctgcaaatga acagtctgag agctgaggat acggccgtat attactgtgc gaaagtctcg   300
taccttagca ccgcgtcctc ccttgactat tggggccaag gtaccctggt caccgtctcg   360
agt                                                                  363
```

METHODS FOR MODIFYING GLYCOSYLATION USING MANGANESE

BACKGROUND

Proteins produced in cell culture can exhibit a high level of heterogeneity. Part of the heterogeneity is due to the glycosylation pattern of the protein (which includes the addition of galactose to certain amino acid residues of the protein). Glycosylation patterns are strongly influenced by cell culture conditions. Different types of glycosylation variants include G0 variants, G1 variants, G2 variants, and high-mannose variants. The variants for example, involve the addition of galactose to an asparagine residue within the amino acid sequence of the recombinant protein, such as in the Fc region of an antibody. The glycosylation (including galactosylation) profile of a particular protein can influence its biological activity due to variable effects on folding, stability, efficacy, and half-life. The glycosylation pattern of a particular protein can be determined by the use of various assays known in the art, such as assays for releasing oligosaccharides present on a particular protein via enzymatic digestion, analysing the variants by chromatography, or other methods in the art.

Glycoproteins are involved in immune defence, cell growth, and cell-cell adhesion, and the glycans that mediate these functions can take on a myriad of complex structures. More than 90% of therapeutic proteins in existence are glycoproteins. For instance, many different recombinant forms of immunoglobulins (e.g., monoclonal antibodies, mAbs) are produced as therapeutic glycoprotein drugs for treating serious conditions. These therapeutic proteins (or glycoproteins) contain complex oligosaccharide moieties whose presence, absence, and profile (i.e. relative proportion of variants present) can have significant impact on therapeutic efficacy, pharmacokinetics, immunogenicity, folding, and stability of the therapeutic protein. For example, certain glycan structures are known to cause aggregation and decrease efficacy of a therapeutic protein. The proportion and pattern of glycosylation variants that are present on a therapeutic protein are a result of the cell culture conditions used in the production of the therapeutic protein. Accordingly, throughout the process of protein production (e.g. fermentation, purification, and formulation) the types and proportions of glycosylation variants present within a population of therapeutic protein should be characterised.

A variety of approaches can be used to characterise glycoproteins and their particular glycan moieties. For example, high-performance liquid chromatography (HPLC) followed by quadrupole time-of-flight mass spectrometry (LC/QTOF MS) can distinguish the number of glycan (such as, galactose) units attached to an intact protein, thus providing the ability to distinguish an active form from an inactive one. In addition, glycosylation sites can be elucidated by digesting the particular glycoprotein with trypsin and using LC/QTOF MS to separate and identify the resulting glycopeptides. Comparison of the masses of these peptides to those generated by a theoretical digestion of the desired glycan form of the protein can determine if the protein is properly glycosylated. Capillary electrophoresis (CE) coupled to QTOF MS can also be used for this purpose.

Analysis of the glycan moieties attached to a protein can also be done by enzymatic deglycosylation and hydrolysis. N-Glycosidase F (PNGase F), an amidase, is used to cleave asparagine-linked (N-linked) oligosaccharides from glycoproteins. Most commonly, the removed glycans are derivatized, labelled, and analysed by fluorescence detection.

Unlabelled glycans can also be analysed by various techniques. Traditionally, high performance anion exchange chromatography with pulsed ampiometric detection (HPAEC-PAD) is used to separate unlabelled glycans based on hydroxyl group interaction with the stationary phase. HPAEC-PAD is also used to determine sialic acid content, which is measured to ensure the product is safe and for batch-to-batch reproducibility. While this method removes the potential issues with labelling efficiency, it still provides fingerprint-like information and requires standards for glycan identification. Gas chromatography (GC) is also frequently used for monosaccharide compositional analysis because it is robust and has high resolution.

In the case of producing a biosimilar, it is imperative that a glycosylation pattern is as close as possible as the reference protein in order that the pharmacokinetics of the biosimilar closely matches those of the reference protein. It is known in the art that the culture conditions and production methods can influence the glycosylation profile of a protein produced in a cell culture method. Various factors in cell culture are inextricably linked, such that merely adding for example, galactose to media may on the one hand favourably influence the galactosylation pattern of the protein but may, on the other hand also have other, negative effects on other characteristics of the protein, such as the charge profile, proportion of protein fragments, proportion of aggregates, and titre protein. Furthermore, cell viability may be affected.

SUMMARY OF THE INVENTION

The present invention provides a cell culture method for adjusting the proportion of G0, G1, G2, and high-mannose galactosylation variants in a population of a recombinant protein produced by a culture of cells in a cell culture medium, the cell culture method comprising: i) initiating the cell culture method in a manganese-free, galactose-free cell culture medium; and ii) supplementing the cell culture medium with manganese at one or more days of the cell culture method duration and wherein the cell culture medium remains galactose free for the cell culture method duration, thereby adjusting the proportion of G0, G1, G2, and high-mannose galactosylation variants in the population of the recombinant protein in comparison to a population of the recombinant protein produced in cell culture that is not supplemented with manganese (Mn) and/or contains galactose.

In embodiments of the present invention, manganese is supplemented in the form of $MnCl_2$. In embodiments of the present invention, the cell culture method is a fed-batch culture method. In embodiments of the present invention, Mn is added to the cell culture medium at one or more of day 3, 4, 5, 6, 7, 8, 9, 10, 11, 12, 13 or 14 of the cell culture method. In embodiments of the present invention, Mn is added at day 3, day 5, day 7 and/or day 10 of the cell culture method. In embodiments of the present invention, the Mn is not added on days 0, 1 or 2 of the cell culture method. In embodiments of the present invention, Mn is added to the culture medium on day 3 to a concentration of about 0.1 μM to about 0.5 μM, in addition to any Mn already present in the cell culture medium. Preferably, Mn is added to the culture medium on day 3 of the cell culture method to a concentration of about 0.14 μM to about 0.325 μM. In embodiments of the present invention, Mn is added to the culture medium on any one of day 5, 7 or day 10 of the cell culture method to a concentration of about 0.5 μM to about 1.0 μM in addition to any Mn already present in the medium. Preferably, Mn is added to the culture medium on any one of day 5, day 7 or day 10 of the cell culture method to a concentration of about 0.75 µM in addition to any Mn already present in the medium. In embodiments of the present invention, Mn is added to the culture medium on day 5, day 7 or day 10 of the cell culture method to a concentration of about 0.2 µM to about 0.4 µM in addition to any Mn already present in the medium. Preferably, Mn is added to the culture medium on day 5, day 7 or day 10 of the cell culture method to a concentration of about 0.29 µM in addition to any Mn already present in the medium.

In embodiments of the present invention, the protein is a TNFα binding protein. In embodiments of the present invention, the TNFα binding protein is an antibody. Preferably, the TNFα binding protein is etanercept, adalimumab, infliximab, or a biosimilar thereof. More preferably, the antibody has: (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

In embodiments of the present invention, the cell culture medium is serum-free and/or protein-free. In embodiments of the present invention, the method further comprises supplementing with asparagine and/or iron.

The present invention also provides a recombinant polypeptide obtainable by any of the above mentioned methods. In embodiments of the present invention, the recombinant polypeptide is an antibody having: (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

In embodiments of the present invention, the galactosylation variants are within the following levels: (i) the level of G0 is within 10% of the G0 level of a reference protein; (ii) the level of G1 is within 10% of the G1 level of a reference protein; (iii) the level of G2 is within 10% of the G2 level of a reference protein; and (iv) the level of high-mannose is within 10% of the high-mannose level of a reference protein.

In embodiments of the present invention, the reference protein is Humira®, and wherein the recombinant polypeptide is an antibody having: (i) a light chain sequence having at least 90% identity with SEQ ID NO:1 and a heavy chain sequence having at least 90% identity with SEQ ID NO:2; (ii) a light chain sequence having at least 95% identity with SEQ ID NO:1 and a heavy chain sequence having at least 95% identity with SEQ ID NO:2; (iii) a light chain sequence of SEQ ID NO:1 and a heavy chain sequence of SEQ ID NO:2; (iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8; (v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8; (vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or (vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

The present invention also provides a pharmaceutical composition comprising any one of the above mentioned recombinant polypeptides.

The present invention also provides a method of making a protein in a cell culture, comprising: i) initiating the cell culture method in a manganese-free, galactose-free cell culture medium; ii) growing a host cell in a cell culture medium, iii) expressing the protein in the host cell, iv) supplementing the cell culture medium with manganese at one or more days of the cell culture method duration and wherein the cell culture medium remains galactose free for the cell culture method duration, thereby adjusting the proportion of G0, G1, G2, and high-mannose galactosylation variants in the population of the recombinant protein in comparison to a population of the recombinant protein produced in cell culture that is not supplemented with manganese and/or contains galactose, and v) purifying the protein from the cell culture.

BRIEF DESCRIPTION OF THE FIGURES

FIG. 1 shows one set of conditions that enable the target proportion of G0, G1, and G2 variants to be reached. In particular FIG. 1 shows the effect of the Mn supplementation, with and without galactose on titre, cell viability and proportion of G0, G1, and G2 galactosylation variants. The biosimilarily corridor is represented by horizontal lines.

DETAILED DESCRIPTION

The present inventors have found that many factors of the cell culture process can influence the glycosylation profile of a protein produced by that cell culture. For example, the addition or lowering of amino acids levels, the addition or lowering of metal ion levels, the temperature, and/or pH at which the cell culture is carried out and the cell culture duration may play a role. Furthermore, the addition or lowering of polysaccharide levels such as levels of galactose can also influence the galactosylation/glycosylation profile of the protein.

The addition of polysaccharides to a protein molecule is an example of a post-translation modification which occurs in the normal production in any protein. In the case of therapeutic proteins the glycosylation patent can have a large influence on the effect of that protein in terms of efficacy, half-life, clearance, immune effect and activity due to factors such as folding and binding. Therefore, when considering the manufacture of a therapeutic protein, and in particular, biosimilars, the galactosylation pattern must be characterised. Therefore, it is important to be able to identify the attributes of the cell culture process that influence certain aspects of the glycosylation process, such as the proportion of G0, G1, G2, and high-mannose variants. For a biosimilar, the proportion of G0, G1, G2, and high-mannose variants must fall within the biosimilarity corridor.

The present inventors have found that the addition of manganese to the cell culture, in the absence of galactose, can positively influence the galactosylation profile of TNFα binding proteins. In particular, these TNFα binding proteins include adalimumab, infliximab, etanercept, and biosimilars thereof. Specifically, the inventors have found that at the beginning of the cell culture method (i.e. on days 0, 1 and 2) the cell culture medium is preferably manganese-free and galactose-free. Manganese added as a separate supplement at certain time points during the cell culture process has the ability to adjust the proportion of G0, G1, G2, and high-mannose galactosylation variants in a population of recombinant protein produced by the culture of cell, in comparison to that where manganese is not included and galactose is included.

The present invention provides a cell culture method for adjusting the proportion of G0, G1, G2, and high-mannose galactosylation variants in a population of a recombinant protein produced by a culture of cells in a cell culture medium, the method comprising i) initiating a cell culture process in a manganese-free, galactose-free cell culture medium; and ii) supplementing the cell culture medium with manganese at one or more days of a cell culture method duration and wherein the cell culture medium remains galactose free for the cell culture method duration, thereby adjusting the proportion of G0, G1, G2, and high-mannose galactosylation variants in the population of the recombinant protein in comparison to a population of the recombinant protein produced in a fed-batch culture that is not supplemented with manganese and/or contains galactose, and wherein the cell culture method duration is up to 17 days long.

The method of the invention is useful in increasing biosimilarity of a protein to a reference protein. A biosimilar is not identical to the reference protein due to many factors, including fact that proteins produced in different mammalian cell lines or under different environmental conditions may be expressed with subtle but important differences with respect to certain characteristics of the protein, e.g. the level of acidic variants, the level of main peak species, the level of basic variants. For this reason biosimilars are never assumed to be exact copies of the reference protein and therefore cannot be directly approved on that basis by authorities, such the Food and Drug Agency (FDA) or the European Medicines Agency (EMA). Provided that a biosimilar can be shown to fall within a "biosimilar corridor" of levels of characteristics of the reference protein, it is generally accepted that the biosimilar is similar enough to the reference protein to gain approval from such authorities. A "biosimilar corridor" is established by testing characteristics of different batch of the reference protein. For example, Humira® manufactured by Abbvie, (adalimumab), was released in 2003 following approval on 31 Dec. 2002. In the intervening years, very slight differences have been found in subsequent batches of Humira® due to usual changes in manufacturing processes and manufacturing sites. By measuring the characteristics of different batches of reference protein, a "biosimilar corridor" is established. Characteristics that are assessed include the level of acidic variants, the level of main peak species, the level of basic variants, the glycosylation variants, aggregates, and fragments of the reference protein. A range of levels associated with each characteristic can be established to build the biosimilar corridor.

By increasing biosimilarity, it is meant that certain characteristics of the protein are brought as close as possible to the characteristics of the reference protein. Such characteristics include, in particular with reference the present invention, the glycosylation pattern of the protein, which comprises the percentage of each glycosylation variant present in a population of a recombinant protein, or biosimilar.

The adjustment of proportion of G0, G1, and G2 may include a decrease in G0 variants, and/or an increase in G1 and/or G2 variants. The adjustment proportion of high-mannose variants may include an increase in high-mannose variants. Such an adjustment may increase the biosimilarity of the recombinant protein to a reference protein having the same amino acid sequence or sequences as the recombinant protein.

In an embodiment of the present invention, the cell culture method is a fed-batch culture method. In an embodiment of the present invention, the Mn is supplemented in the form of MnCl2. In an embodiment of the present invention, the Mn is added to the cell culture medium at one or more of day 3, 4, 5, 6, 7, 8, 9, 10, 11, 12, 13 or 14 of the cell culture method, preferably the Mn is added at day 3, day 5, day 7 and/or day 10 of the cell culture method, and optionally, the Mn may not be added on any one of days 0, 1 or 2. In an embodiment of the present invention, Mn is added to the culture medium on day 3 to a concentration of about 0.1 µM to about 0.5 µM. Mn may be added to the culture medium on day 3 to a concentration of about 0.14 µM to about 0.325 µM; Mn may be added to the culture medium on any one of day 5, 7 or day 10 to a concentration of about 0.25 µM to about 1.0 mM, in addition to any Mn already present in the medium; Mn may be added to the culture medium on any one of day 5, day 7 or day 10 to a concentration of about 0.29 µM to about 0.75 µM, in addition to any Mn already present in the medium.

In an embodiment of the present invention, the protein is an antibody. The antibody may be an anti TNFα antibody, such as adalimumab or infliximab. Alternatively, the protein may be a biosimilar of adalimumab or infliximab.

In an embodiment of the present invention, the cell culture medium is serum-free, and/or protein-free. In an embodiment of the present invention, the cell culture medium is further supplemented with asparagine, and/or iron.

In an embodiment of the present invention, manganese is in the form of manganese chloride ($MnCl_2$) which may be added to the culture medium at one or more of day 3, 4, 5, 6, 7, 8, 9, 10, 11, 12, 13 or 14, i.e. after at least 2 days of manganese-free and galactose-free cell growth. The inventors have surprisingly found that the addition of manganese in the initial cell culture medium, i.e. having manganese present from day 0, has a negative impact on the proportion of G0, G1, G2 and high-mannose variants. The proportion may be adjusted such that each of the variants falls within 20% of the level of variants of a reference protein to which the protein to be produced is compared.

In an embodiment of the present invention, the manganese is added to a concentration of from 0.1 mM to 1 mM. The manganese may be added at a concentration of 0.15, 0.20, 0.25, 0.30, 0.35, 0.40, 0.45, 0.50, 0.55, 0.60, 0.65, 0.70, 0.75, 0.80, 0.85, 0.90, 0.95 mM. This concentration refers to the final concentration of the manganese calculated to be present in the cell culture medium after it has been supplemented with manganese, if the cell culture medium initially contained no manganese prior to supplementation. This concentration does not including any residual manganese that may be left in the media following the previous supplementation. The manganese may be in any acceptable form. In particular, the manganese may be $MnCl_2$. The cell culture media may remain free of manganese prior to day three of the cell culture process and, thereafter, may be added on any one (or more) of days 3 to 14 of the cell culture media.

In an embodiment, the manganese is added at day 3, day 5, day 7 and day 10. During the cell culture process, the cells consume the manganese so that only residual concentrations or no manganese remains in the cell culture medium by the time of the next supplementation. The manganese may be supplemented at different concentration on each of these days or the manganese may be supplemented at the same concentration on one or more of each day.

In an embodiment of the present invention, the cell culture medium is further supplemented with asparagine. The concentration of asparagine may be between 1 mM and 25 mM. The asparagine may be added to a concentration of 5 mM to 20 mM, 10 mM to 15 mM in addition to any Asn already present at that time point. The asparagine may be added to a total amount of 20 to 25 mM over the duration of the cell culture process. The asparagine may be added on one or more of day 0, 1, 2, 3, 4, 5, 6, 7, 8, 9, 10, 11, 12, 13, 14 or 15. The asparagine may be added on day 0, day 3, day 5, day 7, day 10 and/or day 14 of the cell culture process. During the cell culture process, the cells consume the asparagine so that only residual concentrations or no asparagine remains in the cell culture medium by the time of the next supplementation. This concentration refers to the final concentration of the asparagine calculated to be present in the cell culture medium after it has been supplemented with asparagine, if the cell culture medium initially contained no asparagine prior to supplementation. This concentration does not including any residual asparagine that may be left in the media following the previous supplementation.

In an embodiment of the present invention, the cell culture medium is further supplemented with iron. The concentration of iron in the cell culture medium may be between 0.5 mg/L and 5 mg/L. The concentration of iron may be from about 1 mg/L to about 4.5 mg/L, from about 1.5 mg/L to about 4 mg/L, from about 2 mg/L to about 3.5 mg/L or from about 2.5 mg/L to about 3.0 mg/L, in addition to any iron already present in the cell culture medium at that time point. The iron may be added at any one or more of day 0, 1, 2, 3, 4, 5, 6, 7, 8, 9, 10, 11, 12, 13, 14 or 15. The iron may be added on day 0, 3, 5, 7, 10 and/or 14 of the cell culture process. During the cell culture process, the cells consume the iron so that only residual concentrations or no iron remains in the cell culture medium by the time of the next supplementation. This concentration refers to the final concentration of the iron calculated to be present in the cell culture medium after it has been supplemented with iron, if the cell culture medium initially contained no iron prior to supplementation. This concentration does not including any residual iron that may be left in the media following the previous supplementation.

Surprisingly, the inventors have found that galactose is not required in order to increase the addition of galactosylation variants. In fact, it is of benefit to exclude galactose from the cell culture medium and from the feed medium. Galactose was also found to have a negative effect on protein titres and, in some instances, on cell viability. Therefore, it was found to be advantageous to exclude galactose from the cell culture medium and the feed medium of the present invention.

The method of the present invention is particularly useful in the preparation of antibodies including antibodies that are used as therapeutic molecules. In particular, the present invention is relevant for the production of an anti-TN Fa antibody. Embodiments of the anti-TNFα antibody include adalimumab, etanercept, infliximab, and biosimilars thereof. In particular, the adalimumab biosimilar produced by the method of the present invention has a proportion of G0, G1, G2, and high-mannose galactosylation variants within 20%, 10%, 5%, 2% or 1% of the proportional levels of the G0, G1, G2, and high-mannose variants of Humira®, as a reference protein.

The present invention may adjust the proportion of galactosylation variants to within the following levels: (i) the level of G0 is within 10% of the G0 level of a reference protein; (ii) the level of G1 is within 10% of the G1 level of a reference protein; (iii) the level of G2 is within 10% of the G2 level of a reference protein; and (iii) the level of high-mannose is within 10% of the high-mannose level of a reference protein.

As used herein, "adalimumab" refers to any human monoclonal antibody that specifically binds TNFα having the light chain sequence of SEQ ID NO:1 and the heavy chain sequence of SEQ ID NO:2. Adalimumab is sold under the trade name Humira® and has CAS designation number 331731-18-1.

As used herein, "etanercept" refers to any fusion protein that inhibits a TNFα, is sold under the trade name Enbrel®, and has Chemical Abstracts Service (CAS) designation number 185243-69-0.

As used herein, "infliximab" refers to any chimeric monoclonal antibody that specifically binds to TNFα, is sold under the trade names Remicade®, Remsima®, and/or Inflectra®, and has CAS designation number 170277-31-3.

As used herein, "biosimilar" (of an approved reference product/biological drug, such as a protein therapeutic, antibody, etc.) refers to a biologic product that is highly similar to a reference product notwithstanding minor differences in clinically inactive components having no clinically meaningful differences between the biological product and the reference product in terms of the safety, purity, and potency of the product. In one embodiment, the biosimilar biological product is biosimilar refers to a biologic product that is similar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biological product. In one embodiment, the biosimilar biological product and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biological product are the same as those of the reference product. In one embodiment, the facility in which the biological product is manufactured, processed, packed, or held meets standards designed to assure that the biological product continues to be safe, pure, and potent. The reference product may be approved in at least one of the U.S., Europe, or Japan.

As used herein, the terms "about" and "approximately", as applied to one or more particular cell culture conditions or to the level of misincorporation, refer to a range of values that are similar to the stated reference value for that culture condition or misincorporation level. The term "about" may refer to a range of values that fall within 10%, 9%, 8%, 7%, 6%, 5%, 4%, 3%, 2%, 1%, 0.5%, or 0.05% of the stated reference value for that culture condition or misincorporation level.

The term "amino acid" as used herein refers to any of the twenty naturally occurring amino acids that are normally used in the formation of polypeptides, or analogs or derivatives of those amino acids as understood by the skilled person. Amino acids of the present invention are provided in medium to cell cultures. The amino acids provided in the medium may be provided as salts or in hydrate form.

The term "antibody" is used as understood in the art, i.e. an immunoglobulin molecule that recognises and specifically binds to a target, such as a protein, polypeptide, peptide, carbohydrate, polynucleotide, lipid, or combinations of the foregoing etc., through at least one antigen recognition site within the variable region of the immunoglobulin molecule. The term encompasses, as understood in the art, intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of IgA, IgD, IgE, IgG, and IgM, and include, for example IgG1, IgG2, IgG3, IgG4, IgA1 and IgA2.

The term "cell culture medium" as used herein refers to any cell culture medium used to culture cells that has not been modified either by supplementation, or by selective removal of a certain component.

The term "batch culture" as used herein refers to a method of culturing cells in which all the components that will ultimately be used in culturing the cells, including the medium as well as the cells themselves, are provided at the beginning of the culturing process i.e. day 0. A batch culture is typically stopped at some point and the cells and/or components in the medium are harvested and optionally purified.

The term "bioreactor" as used herein refers to any vessel used for the growth of a mammalian cell culture. The bioreactor can be of any size so long as it is useful for the culturing of mammalian cells. Typically, the bioreactor will be at least 1 liter and may be 10, 100, 250, 500, 1000, 2500, 5000, 8000, 10,000, 12,000, 15,000 litres or more, or any volume in between. The internal conditions of the bioreactor are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or protein of interest. The volume of the large-scale cell culture production bioreactor is typically at least 500 liters and may be 1000, 2000, 2500, 5000, 8000, 10,000, 12,0000 liters or more, or any volume in between. One of ordinary skill in the art will be aware of and will be able to choose suitable bioreactors for use in practicing the present invention.

The term "cell density" as used herein refers to that number of cells present in a given volume of medium.

The terms "culture", "cell culture" and "eukaryotic cell culture" as used herein refer to a eukaryotic cell population that is suspended in a medium under conditions suitable to survival and/or growth of the cell population. As will be clear to those of ordinary skill in the art, these terms as used herein may refer to the combination comprising the mammalian cell population and the medium in which the population is suspended.

The term "fed-batch culture" as used herein refers to a method of culturing cells in which additional components are provided to the culture at some time subsequent to the beginning of the culture process i.e. after day 0. The provided components typically comprise nutritional supplements for the cells which have been depleted during the culturing process. A fed-batch culture is typically stopped at some point and the cells and/or components in the medium are harvested and optionally purified.

"Growth phase" of the cell culture refers to the period of exponential cell growth (the log phase) where cells are generally rapidly dividing. During this phase, cells are cultured for a period of time, usually between 1-4 days, and under such conditions that cell growth is maximized. The determination of the growth cycle for the host cell can be determined for the particular host cell envisioned without undue experimentation. For a particular cell line, the period of time and conditions are determined to be optimal for cell growth and division. During the growth phase, cells are cultured in nutrient medium containing the necessary additives, in a controlled atmosphere, such that optimal growth is achieved for the particular cell line. Cells are maintained in the growth phase for a period of about between one and four days, usually between two to three days.

"Production phase" of the cell culture refers to the period of time during which cell growth has plateaued. During the production phase, logarithmic cell growth has ended and protein production is primary. During this period of time the medium is generally supplemented to maintain cell stability.

The term "expression" or "expresses" are used herein to refer to transcription and translation occurring within a host cell. Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

The terms "medium", "cell culture medium", "culture medium", and "growth medium" as used herein refer to a solution containing nutrients which nourish growing eukaryotic cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. The medium may also be a "defined medium" such as a serum-free medium and/or protein free medium that contains no proteins, hydrolysates or components of unknown composition. Defined media are free of animal-derived components and all components have a known chemical structure.

The terms "protein" as used herein refers to a sequential chain of amino acids linked together via peptide bonds, also referred to interchangeably with the term "polypeptide". The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit. If discrete functional unit is comprised of more than one polypeptide that physically associate with one another, the term "protein" as used herein refers to the multiple polypeptides that are physically coupled and function together as the discrete unit, such as an antibody.

"Recombinantly expressed polypeptide" and "recombinant polypeptide protein" as used herein refer to a polypeptide expressed from a mammalian host cell that has been genetically engineered to express that polypeptide. The recombinantly expressed polypeptide can be identical or similar to polypeptides that are normally expressed in the mammalian host cell. The recombinantly expressed polypeptide can also be foreign to the host cell (i.e. exogenous). Alternatively, the recombinantly expressed polypeptide can be chimeric in that portions of the polypeptide contain amino acid sequences that are identical or similar to polypeptides normally expressed in the mammalian host cell, while other portions are foreign to the host cell.

The term "titre" as used herein refers to the total amount of recombinantly expressed polypeptide or protein produced by a mammalian cell culture divided by a given amount of medium volume. Titre is typically expressed in units of milligrams of polypeptide or protein per milliliter of medium.

As used herein, the singular forms "a", "an", and "the" include plural forms unless the context clearly dictates otherwise.

It is understood that whenever embodiments are described herein with the language "comprising" otherwise analogous embodiments described in terms of "consisting" and/or "consisting essentially of" are also provided.

Those of ordinary skill in the art will understand that various modifications to these preferred embodiments are within the scope of the appended claims. It is the claims and equivalents thereof that define the scope of the present invention, which is not and should not be limited to or by this description of certain preferred embodiments.

Any polypeptide or protein that is expressible in a host cell may be produced in accordance with the method of the present invention. The polypeptide is preferably expressed from a gene that is introduced into the host cell through genetic engineering, i.e. a recombinant polypeptide. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Of particular relevance to the present invention is the production of antibodies. Antibodies are proteins that have the ability to specifically bind a particular antigen. Any antibody that can be expressed in a host cell may be used in accordance with the present invention. In one embodiment, the antibody to be expressed is a monoclonal antibody.

Particular antibodies can be made, for example, by preparing and expressing synthetic genes that encode the recited amino acid sequences or by mutating human germ line genes to provide a gene that encodes the recited amino acid sequences. Moreover, these antibodies can be produced by any method known to one of skill in the art.

In one embodiment, the methods of the invention are used to produce protein that specifically binds a tumour-necrosis factor alpha (TNFα). Embodiments of the protein include adalimumab, etanercept, infliximab, and biosimilars thereof. Preferably, the protein is an antibody and more preferably the antibody is an adalimumab biosimilar.

In an embodiment, the antibody has (i) a light chain sequence having at least 90% identity with SEQ ID NO:1 and a heavy chain sequence having at least 90% identity with SEQ ID NO:2, or (ii) a light chain sequence having at least 95% identity with SEQ ID NO:1 and a heavy chain sequence having at least 95% identity with SEQ ID NO:2, or (iii) a light chain sequence of SEQ ID NO:1 and a heavy chain sequence of SEQ ID NO:2, In embodiments of the present invention, the antibody is adalimumab. In embodiments of the present invention, the antibody is a biosimilar of adalimumab. In embodiments of the present invention, the antibody has a light chain sequence comprising SEQ ID NO: 3, SEQ ID NO: 5, and SEQ ID NO: 7; and the antibody has a heavy chain sequence comprising SEQ ID NO: 4, SEQ ID NO: 6, and SEQ ID NO: 8. In embodiments of the present invention, the antibody has a light chain sequence comprising SEQ ID NO: 3, wherein Xaa of SEQ ID NO: 3 is any naturally occurring amino acid; and has a heavy chain sequence comprising SEQ ID NO: 4, wherein Xaa of SEQ ID NO: 4 is any naturally occurring amino acid. In embodiments of the present invention, Xaa of SEQ ID NO: 3 is Threonine or Alanine. In embodiments of the present invention, Xaa of SEQ ID NO: 4 is Tyrosine or Asparagine.

In one embodiment, the antibody is an antigen-binding fragment of a full length antibody, e.g., a Fab, F(ab')2, Fv or a single chain Fv fragment. Typically, the antibody is a full length antibody. The antibody can be a monoclonal antibody or a mono-specific antibody. The antibody may be a human, humanized, CDR-grafted, chimeric, mutated, affinity matured, deimmunized, synthetic or otherwise in vitro-generated antibody, and combinations thereof.

Any mammalian cell or cell type susceptible to cell culture, and to expression of polypeptides, may be utilized in accordance with the present invention as known in the art. In one embodiment, the method of the present invention is applied in the culturing of and expression of polypeptides from CHO cell lines. In one embodiment, the cell line is CHO-2. Additionally, any number of commercially and non-commercially available hybridoma cell lines that express polypeptides or proteins may be utilized in accordance with the present invention.

The mammalian cell culture of the method of the present invention may be prepared in any medium suitable for the particular cell being cultured. Commercially available media such as Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions, as well as any media that are well known to the person skilled in the art. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and glucose or an equivalent energy source. Any other necessary supplements may also be included at appropriate concentrations that would be known to those skilled in the art.

In the present invention, the medium is supplemented with manganese and optionally with asparagine and/or iron. Additional amino acids and nutrients may also be used in accordance with standard cell culture techniques as known to the skilled person, for example to replenish essential amino acids as the cells multiply, replenish an energy source and replenish other essential micronutrients, such as trace elements.

The amount of supplementation required can vary depending on the cellular growth conditions. For example, factors that influence cellular consumption rates, will affect the amount of supplementation that is required to prevent misincorporation. Such factors include, but are not limited to, temperature, osmolality, and pH, as known in the art.

The basal cell culture medium, i.e. the medium in which the cell culture is started, prior to any additional supplementation may contain essential amino acids, vitamins (such as folic acid, biotin, thiamine), salts (such as sodium chloride, sodium bicarbonate), metal ions (such as, in the terms of cupric sulphate, Ferric ammonium citrate), foaming agents (such as Pluronic®), and an energy source (such as glucose or sucrose). The particular combination and amounts of each component may vary depending on the cell line, and the recombinant protein to be produced.

Various methods of preparing mammalian cells for production of proteins or polypeptides by fed-batch culture are well known in the art. Generally, the cells are first propagated or expanded in a step-wise procedure until a cell density is reached that is suitable for inoculating the bioreactor in which the method of the invention is to take place.

Such methods of propagation or expansion can be carried out by any of the variety of methods well-known to one of ordinary skill in the art.

In accordance with the present invention, the culture size can be any volume that is appropriate for production of polypeptides. In one embodiment, the volume of the production bioreactor is at least 500 liters. In other preferred embodiments, the volume of the production bioreactor is 1000, 2000, 2500, 5000, 8000, 10000, 12000 or 15000 litres or more, or any volume in between. One of ordinary skill in the art will be aware of and will be able to choose a suitable culture size for use in practicing the present invention.

In accordance with the present invention, the cells are allowed to grow for a defined period of time, i.e. this is the duration of the cell culture method. For example, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more. The method of the present invention may involve maintaining the cell culture for a duration of 14 or 17 days.

In accordance with the present invention, the cells may be maintained in the subsequent production phase (after the lag phase) until a desired cell density or protein titre is reached. In one embodiment, the cells are maintained in the subsequent production phase until the titre to the recombinant polypeptide or protein reaches a maximum. In other embodiments, the culture is harvested prior to this point. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density.

The cells may be allowed to grow for a defined period of time during the subsequent production phase.

An increased concentration of the amino acids may be added in the basal media prior to the cell culture process (i.e. at day 0) or else supplemented in the feed media in the fed-batch system, on any one or more of day 1, 2, 3, 4, 5, 6, 7, 8, 9, 10, 11, 12, 13 or 14.

In embodiments of the present invention, the cell culture is supplemented during the growth and/or subsequent production phase with nutrients or other medium components that have been depleted or metabolized by the cells. Alternatively or additionally, it may be beneficial or necessary to supplement the cell culture prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, glucose, or other energy source. These supplementary components, including amino acids, may be added to the cell culture all at one time, or may be provided to the cell culture in a series of additions. The supplementary components may be provided to the cell culture at multiple times in proportional amounts. It may be desirable to provide only certain of the supplementary components initially, and provide the remaining components at a later time. The cell culture may be fed at regular intervals with the same concentrations of these supplementary components.

In embodiments of the present invention, the total volume added to the cell culture should optimally be kept to a minimal amount. In embodiments of the present invention, the total volume of the medium or solution containing the supplementary components added to the cell culture is 1, 2, 3, 4, 5, 6, 7, 8, 9, 10, 15, 20, 25, 30, 35, 40, 45, or 50% of the volume of the cell culture prior to providing the supplementary components.

In general, it will typically be desirable to isolate and/or purify proteins or polypeptides produced by the method according to the present invention. The expressed polypeptide or protein is secreted into the medium and thus cells and other solids may be removed, as by centrifugation or filtering for example, as a first step in the purification process. Further purification may be carried out by any method known to the skilled person.

The present invention also provides a recombinant polypeptide produced by any one of the methods described above. In embodiments of the present invention, the recombinant polypeptide is adalimumab or a biosimilar thereof. The recombinant polypeptide may have a proportion of G0, G1, G2, and high-mannose galactosylation variants within 10% of the proportional levels of the reference protein (Humira®). For example, if the whole population of reference protein contains G0 galactosylation variants then the reference protein would be said to contain 100% G0 galactosylation variants. For the recombinant polypeptide of the invention to be within 10% of this level, recombinant polypeptide produced by the method would contain at least 90% G0 galactosylation variants.

Once purified, the protein or polypeptide (for example an antibody such as an anti-TNFα antibody described herein) can be formulated as a pharmaceutical composition for administration to a subject, e.g., to treat a disorder, such as an autoimmune disorder or disease. Thus, a pharmaceutical composition comprising the recombinant polypeptide of the second aspect is also provided.

The foregoing description is to be understood as being representative only and is not intended to be limiting. Alternative methods and materials for implementing the invention and also additional applications will be apparent to one of skill in the art, and are intended to be included within the accompanying claims.

The invention is described below with reference to the following non-limiting Examples and FIGURE.

EXAMPLES

All examples related to the production of an adalimumab biosimilar.

Example 1

The addition of various concentrations of galactose was tested in order to try to decrease G0 forms. The results of these experiments are shown in table 1.

TABLE 1

| Day 14 | G0 | G1 | G2 | Hi Man |
|---|---|---|---|---|
| (day 0 + main feed) | 89.1 | 10.4 | 0.6 | 5.9 |
| (day 0 + main feed) +10 mM Gal | 88.1 | 11.5 | 0.5 | 5.3 |
| (day 0 + main feed) +20 mM Gal | 84.6 | 14.6 | 0.7 | 4.7 |
| (day 0 + main feed) +20 mM Gal, no pH shift | 89.4 | 10.1 | 0.5 | 5.8 |
| (day 0 + daily) | 89.8 | 9.6 | 0.6 | 5.8 |
| RUN 1 (Process F) | 74.9 | 22.3 | 2.8 | 4.6 |
| Ctrl (Process F) | 73.2 | 24.4 | 2.3 | 3.6 |
| RUN 1 (Process F) | 79.3 | 19.0 | 1.7 | 4.8 |
| 5000L RUN 1 (Process F) | 84.3 | 14.9 | 0.8 | 5.5 |

| Day 16 | G0 | G1 | G2 | Hi Man |
|---|---|---|---|---|
| (day 0 + main feed) | 89.8 | 9.6 | 0.6 | 7.5 |
| (day 0 + main feed) +10 mM Gal | 88.7 | 10.8 | 0.5 | 6.1 |
| (day 0 + main feed) +20 mM Gal | 85.4 | 13.8 | 0.8 | 5.8 |
| (day 0 + main feed) +20 mM Gal, no pH shift | 89.6 | 9.9 | 0.6 | 7.5 |
| (day 0 + daily) | 90.1 | 9.1 | 0.8 | 7.5 |
| RUN 1 (Process F) | 79.2 | 19.4 | 1.3 | 5.8 |
| Ctrl (Process F) | 75.3 | 22.6 | 2.1 | 6.5 |
| RUN 1 (Process F) | 82.3 | 16.5 | 1.2 | 5.3 |
| 5000L RUN 1 (Process F) | 86.3 | 12.8 | 0.9 | 6.3 |
| RMP comparability limits (corridor) | 76.7-81.6 | 17.1-21.0 | 1.1-2.4 | 3.4-9.9 |

| Day 17 | G0 | G1 | G2 | Hi Man |
|---|---|---|---|---|
| (day 0 + main feed) | 90.0 | 9.1 | 0.8 | 6.9 |
| (day 0 + main feed) +10 mM Gal | 89.2 | 10.3 | 0.5 | 6.1 |
| (day 0 + main feed) +20 mM Gal | 86.1 | 13.3 | 0.6 | 6.4 |
| (day 0 + main feed) +20 mM Gal, no pH shift | 89.9 | 9.6 | 0.5 | 6.6 |
| (day 0 + daily) | 91.0 | 8.6 | 0.5 | 6.4 |
| RUN 1 (Process A2) | 80.1 | 18.2 | 1.7 | 5.8 |
| Ctrl (Process F) | 77.1 | 21.1 | 1.8 | 4.8 |
| RUN 1 (Process F) | 83.1 | 15.7 | 1.3 | 5.6 |
| 5000L RUN 1 (Process F) | 87.3 | 12.1 | 0.6 | 6.5 |
| RMP comparability limits (corridor) | 76.7-81.6 | 17.1-21.0 | 1.1-2.4 | 3.4-9.9 |

Globally, the addition of galactose to cultures was not able to prevent the increase in G0 forms and only moderately increased G1 forms. Regarding Run 1, all G forms and high mannose forms were within the biosimilarity corridor on day 12, but afterwards, G0 forms increased and were outside comparability limits. High mannose forms were within RMP (reference protein) comparability limits for all conditions tested between day 12 and 17. On day 17, one satellite run was within RMP comparability limits while the other one had too many G0 forms and too few G1 forms.

Therefore, it can be seen that the simple addition of galactose cannot favourably adjust the proportionate levels of G0, G1 and G2 galactosylation variants.

Example 2

As shown in previous experiment, the addition of extra galactose cultures failed to adjust the galactosylation profile. Therefore, Mn was tested in replacement of or in combination to galactose supplementation in the main feed. Test conditions are shown in Table 2.

TABLE 2

| Runs | Main Feed (day 3, 5, 7, 10, 14) |
|---|---|
| Ctrl | |
| increased agitation | |
| no Gal, Mn 4 µM | +MnCl₂ 16.67 µM |
| no Gal, Mn 1.2 µM | +MnCl₂ 5 µM |
| no Gal, Mn 0.12 µM | +MnCl₂ 0.5 µM |
| Gal 11 mM, Mn 1.2 µM | nCl₂ 5 µM |
| Gal 11 mM, Mn 0.4 µM | +MnCl₂ 1.67 µM |
| Gal 11 mM, Mn 0.12 µM | +MnCl₂ 0.5 µM |

Figure 1:
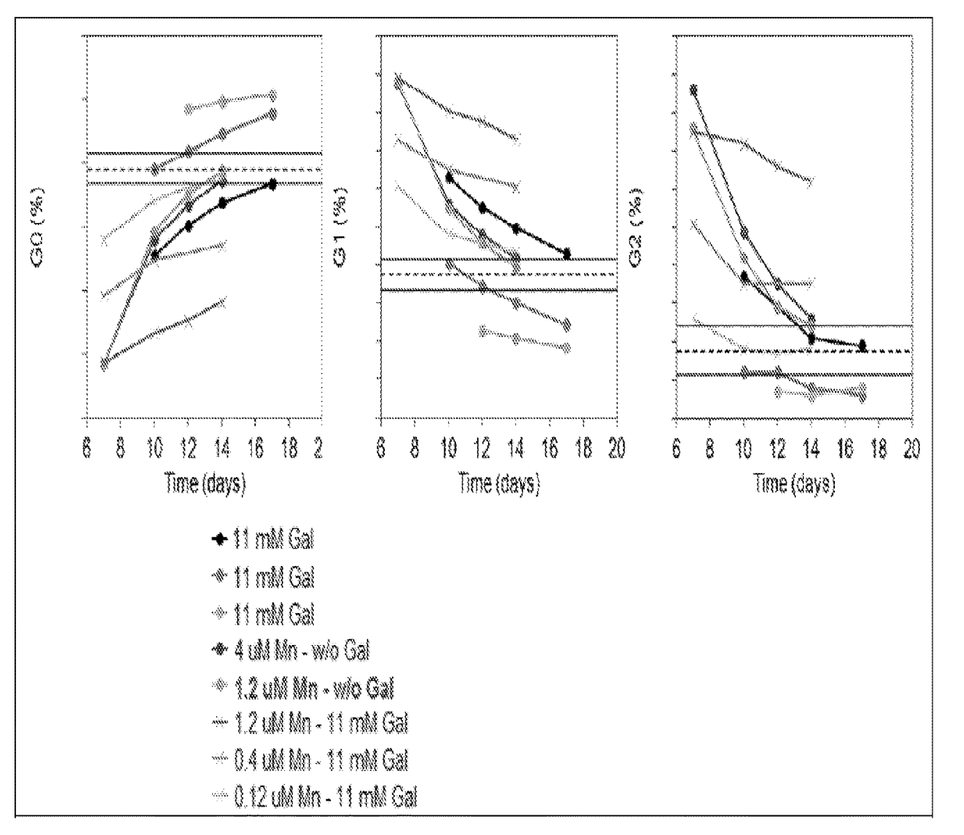

FIG. 1 shows the effect of the Mn supplementation, with and without galactose on titre, cell viability and proportion of G0, G1 and G2 galactosylation variants. The biosimilarity corridor is represented by horizontal lines. Results are also shown in table 3

TABLE 3

| Day 14 | G0 | G1 | G2 | Hi Man |
|---|---|---|---|---|
| Ctrl | x | x | x | ✓ |
| Increased agitation | N/A | N/A | N/A | N/A |
| no Gal Mn 4 µM | ✓ | ✓ | ✓ | ✓ |
| no Gal Mn 1.2 µM | ✓ | ✓ | ✓ | ✓ |
| no Gal Mn 0.12 µM | x | x | ✓ | ✓ |
| Gal 11 mM, Mn 1.2 µM | x | x | x | x |
| Gal 11 mM, Mn 0.4 µM | x | x | x | ✓ |
| Gal 11mM, Mn 0.12 µM | ✓ | x | ✓ | ✓ |
| RMP comparability limits | 76.7-81.6 | 17.1-21.0 | 1.1-2.4 | 3.4-9.9 |

✓ means that the results fall within the biosimilarity corridor (the RMP comparability limits)
x means that the results do not fall within the biosimilarity corridor (the RMP comparability limits)

The addition of Mn to the process decreased G0 and increased G1 and G2 forms as expected. Two conditions enabled to be within the biosimilarity corridor for galactosylation on day 14: Mn 4 μM and Mn 1.2 μM, both without Gal. Under these conditions, high mannose forms were also within the biosimilarity corridor.

Culture supplementation with Mn enabled to modulate galactosylation. Galactosylation was highly time dependent.

The addition of Mn 1.2 μM or 4 μM in the absence of Gal enabled to have a galactosylation profile within the biosimilarity corridor on day 14. High mannose forms were also within the biosimilarity corridor under these conditions.

Best final titers were obtained with 1.2 and 4 μM of Mn and no galactose.

What is claimed is:

1. A cell culture method for adjusting the proportion of G0, G1, G2, and high-mannose glycosylation variants in a population of a recombinant protein produced by a culture of cells in a cell culture medium, the cell culture method comprising:
   i) initiating the cell culture method in a manganese-free, galactose-free cell culture medium; and
   ii) supplementing the cell culture medium with manganese (Mn) at one or more days of the cell culture method duration and wherein the cell culture medium remains galactose free for the cell culture method duration, thereby adjusting the proportion of G0, G1, G2, and high-mannose glycosylation variants in the population of the recombinant protein in comparison to a population of the recombinant protein produced in cell culture that is not supplemented with manganese and/or contains galactose.

2. The method of claim 1, wherein the Mn is supplemented in the form of $MnCl_2$.

3. The method of claim 1 wherein the cell culture method is a fed-batch culture method.

4. The method of claim 1, wherein the Mn is added to the cell culture medium at one or more of day 3, 4, 5, 6, 7, 8, 9, 10, 11, 12, 13 or 14 of the cell culture method.

5. The method of claim 1, wherein Mn is added at day 3, day 5, day 7 and/or day 10 of the cell culture method.

6. The method of claim 1, wherein the Mn is not added on days 0, 1 or 2 of the cell culture method.

7. The method of claim 1, wherein Mn is added to the culture medium on day 3 of the cell culture method to a concentration of about 0.14 μM to about 0.325 μM.

8. The method of claim 1, wherein Mn is added to the culture medium on any one of day 5, day 7 or day 10 of the cell culture method to a concentration of about 0.75 μM or about 0.29 μM in addition to any Mn already present in the medium.

9. The method of claim 1, wherein the protein is a TNFα binding protein.

10. The method of claim 9, wherein the TNFα binding protein is etanercept, adalimumab, infliximab, or a biosimilar thereof.

11. The method of claim 9, wherein the TNFα binding protein is an antibody.

12. The method of claim 11, wherein the antibody has:
(i) a light chain sequence having at least 90% identity with SEQ ID NO:1 and a heavy chain sequence having at least 90% identity with SEQ ID NO:2;
(ii) a light chain sequence having at least 95% identity with SEQ ID NO:1 and a heavy chain sequence having at least 95% identity with SEQ ID NO:2;
(iii) a light chain sequence of SEQ ID NO:1 and a heavy chain sequence of SEQ ID NO:2;
(iv) a light chain sequence comprising SEQ ID NO: 3, SEQ ID NO: 5, and SEQ ID NO: 7; and a heavy chain sequence comprising SEQ ID NO: 4, SEQ ID NO: 6, and SEQ ID NO: 8;
(v) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8;
(vi) a light chain sequence comprising SEQ ID NO: 3, SEQ ID NO: 5, and SEQ ID NO: 7, and a heavy chain sequence comprising SEQ ID NO: 4, SEQ ID NO: 6, and SEQ ID NO: 8, wherein Xaa of SEQ ID NO: 4 is Tyrosine or Asparagine; or
(vii) a light chain sequence comprising SEQ ID NO: 3, SEQ ID NO: 5, and SEQ ID NO: 7, wherein Xaa in SEQ ID NO:3 is Threonine or Alanine, and a heavy chain sequence comprising SEQ ID NO: 4, SEQ ID NO: 6, and SEQ ID NO: 8, wherein Xaa of SEQ ID NO: 4 is Tyrosine or Asparagine.

13. The method of claim 1, wherein the cell culture medium is serum-free and/or protein-free.

14. The method of claim 1, further comprising supplementing with asparagine and/or iron.

15. A method of making a recombinant protein in a cell culture, comprising:
i) initiating the cell culture method in a manganese-free, galactose-free cell culture medium;
ii) growing a host cell in a cell culture medium,
iii) expressing the recombinant protein in the host cell,
iv) supplementing the cell culture medium with manganese at one or more days of the cell culture method duration and wherein the cell culture medium remains galactose free for the cell culture method duration, thereby adjusting the proportion of G0, G1, G2, and high-mannose glycosylation variants in the population of the recombinant protein in comparison to a population of the recombinant protein produced in cell culture that is not supplemented with manganese and/or contains galactose, and
v) purifying the recombinant protein from the cell culture.

* * * * *